United States Patent [19]

Pugin et al.

[11] Patent Number: 5,252,751
[45] Date of Patent: Oct. 12, 1993

[54] DIPHOSPHINES CONTAINING SILANE GROUPS, IMMOBILISED DIPHOSPHINES AND THE USE THEREOF AS HYDROGENATION CATALYSTS

[75] Inventors: Benoit Pugin, Münchenstein; Felix Spindler, Starrkirch-Wil; Manfred Müller, Dagmersellen, all of Switzerland

[73] Assignee: Ciba-Geigy Corporation, Ardsley, N.Y.

[21] Appl. No.: 823,516

[22] Filed: Jan. 21, 1992

[30] Foreign Application Priority Data

Jan. 25, 1991 [CH] Switzerland ............... 218/91

[51] Int. Cl.$^5$ ............... C07F 7/08; C07F 9/28
[52] U.S. Cl. ............... 549/214; 549/221
[58] Field of Search ............... 549/221, 214, 430

[56] References Cited

U.S. PATENT DOCUMENTS

| | | | |
|---|---|---|---|
| 4,994,615 | 2/1991 | Spindler et al. | 564/304 |
| 4,996,361 | 2/1991 | Cullen et al. | 564/304 |
| 5,011,995 | 4/1991 | Pugin et al. | 564/302 |

OTHER PUBLICATIONS

*Advanced Organic Chemistry*, 3rd Edition, J. March, pp. 802-803, 1985.
"Acylation by Ketens and Isocyanates A Mechanistic Comparison", by D. P. N. Satchell, *Chem. Soc. Rev., vol. 4 No. 1, 1975, pp. 231-245.*
Achiwa, J. Chem. Jap. Soc., Chem. Letters, pp. 905-908 (1978).
Nagel, et al.; J. Chem. Soc., Chem. Commun., pp. 1098-1099 (1986).
Kolb, et al., React Kiret. Catal. Let. 7(2), pp. 199-204 (1977).

*Primary Examiner*—Alan L. Rotman
*Assistant Examiner*—D. Margaret M. Mach
*Attorney, Agent, or Firm*—Kevin T. Mansfield; Edward McC. Roberts

[57] ABSTRACT

Compounds of formula I

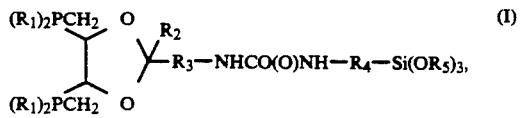

wherein $R_1$ denotes identical or different radicals and is linear or branched $C_1$-$C_{12}$alkyl, unsubstituted $C_5$-$C_6$cycloalkyl or $C_5$-$C_6$cycloalkyl which is substituted by $C_1$-$C_4$alkyl or $C_1$-$C_4$alkoxy, or is phenyl or benzyl, or both substituents $R_1$ of a group $(R_1)_2P$ are o,o'-diphenylene, $R_2$ is hydrogen, linear or branched $C_1$-$C_{12}$alkyl, phenyl or benzyl, $R_3$ is $C_1$-$C_{12}$alkylene, $R_4$ is $C_2$-$C_{18}$alkylene, phenylene or benzylene, and $R_5$ is $C_1$-$C_6$alkyl or phenyl, can be applied to solid carriers, such as silica gel or aerosils, and complexed with rhodium or iridium compounds. These materials are heterogeneous and separable catalysts for the asymmetrical hydrogenation of prochiral compounds containing carbon double bonds or carbon/hetero atom double bonds, for example ketones and imines.

8 Claims, No Drawings

DIPHOSPHINES CONTAINING SILANE GROUPS, IMMOBILISED DIPHOSPHINES AND THE USE THEREOF AS HYDROGENATION CATALYSTS

The present invention relates to dioxalane diphosphines which contain silane groups, to said dioxalane diphosphines fixed on a solid carrier material and to the use thereof in the form of rhodium or iridium complexes for the hydrogenation of olefinic double bonds and hetero double bonds, especially for enantioselective hydrogenation using chiral pyrrolidine diphosphines.

The enantioselective hydrogenation of ketimines to optically active secondary amines using chiral rhodium and iridium diphosphine complexes as homogeneous catalysts is described in U.S. Pat. No. 4,994,615, EP-A-0 302 021 and EP-A-301 457. The expensive catalysts cannot, however, be recovered, or recovery is only possible by complicated separating methods and always with unwanted losses. Moreover, these cyalysts lose much of their activity in the course of the first reaction, so that their direct reuse in further hydrogenation processes is allied to high losses of yield and is therefore uneconomic. There is a need for catalysts which can be readily separated and reused while substantially retaining their activity and, in particular, their selectivity.

In J. Chem. Japan. Soc., Chemistry Letters, pages 905 to 908 (1978), K. Achiwa describes polystyrene copolymers whose benzene rings contain pyrrolidine diphosphine-N-carbonyl aroups complexed with rhodium. It is difficult to synthesise these monomers, and the hydrogenation of prochiral olefins with these heterogeneous catalysts entails a loss of enantioselectivity.

U. Nagel et al. disclose heterogeneous rhodium catalysts for the enantioselective hydrogenation of α-(acetylamino)cinnamic acid in J. Chem. Soc., Chem. Commun., pages 1098-1099. The catalystas are pryrrolidine diphosphines which are complexed with rhodium and which carry a triethoxysilyl-n-propyldicarboxylic acid monoamide radical at the N-atom. They are applied to silica gel as solid carrier material. The synthesis of these materials is very troublesome. Although comparably good selectivities are obtained as compared with the monomers, the loss of activity is high and diminishes the possibility of reuse.

I. Kolb et al. describe in React. Kinet. Catal. Lett. 7(2), pages 199 to 204 (1977) chiral heterogeneous rhodium catalysts which are applied to silica gel as solid carrier. 2,3-(5'-Triethoxysilyl-2'-pentylidenedioxyl)-1,4-bis(diphenylphosphino)butane is used as chiral complexing agent which can be fixed on a solid carrier. In the hydrogenation of α-acetamidocinnamic acid, a substantial loss of activity and selectivity is observed as compared with the monomeric rhodium catalysts.

In one of its aspects, the invention relates to compounds of formula I

(I)

wherein $R_1$ denotes identical or different radicals and is linear or branched $C_1$-$C_{12}$alkyl, unsubstituted $C_5$-$C_6$cycloalkyl or $C_5$-$C_6$cycloalkyl which is substituted by $C_1$-$C_4$alkyl or $C_1$-$C_4$alkoxy, or is phenyl or benzyl, or both substituents $R_1$ of a group $(R_1)_2P$ are o,o'-diphenylene, $R_2$ is hydrogen, linear or branched $C_1$-$C_{12}$alkyl, phenyl or benzyl, $R_3$ is $C_1$-$C_{12}$alkylene, $R_4$ is $C_2$-$C_{18}$alkylene, phenylene or benzylene, and $R_5$ is $C_1$-$C_6$alkyl or phenyl.

$R_1$ an alkyl contains preferably 1 to 8, most preferably 1 to 4, carbon atoms. Alkyl is typically methyl, ethyl and the isomers of propyl, butyl, pentyl, hexyl, heptyl, octyl, nonyl, decyl, undecyl and dodecyl. Particularly suitable alkyl and alkoxy substituents are methyl, ethyl, methoxy and ethoxy. Cycloalkyl is typically cyclopentyl and cyclohexyl. In a particularly preferred embodiment of the invention, $R_1$ is phenyl.

$R_2$ as alkyl contains preferably 1 to 6 and, most preferably, 1 to 4, carbon atoms. Examples have been cited above in connection with $R_1$. In a preferred embodiment of the compounds of the invention $R_2$ is hydrogen, methyl, ethyl, n- or isopropyl, or n-, iso- or tert-butyl.

$R_3$ as alkylene may be linear or branched and contains preferably 1 to 8 and, most preferably, 1 to 6, carbon atoms. Illustrative examples are methylene, ethylene, 1,2- and 1,3-propylene, 1,2-, 1,3- and 1,4-butylene and the isomers of pentylene, hexylene, heptylene, octylene, nonylene, decylene, undecylene and dodecylene. Particularly preferred alkylene radicals are ethylene, 1,2-propylene, 1,3-propylene, 1,2-, 1,3- and 1,4-butylene, 1,2-, 1,3-, 1,4- and 1,5-pentylene and 1,2-, 1,3-, 1,4-, 1,5- and 1,6-hexylene.

$R_4$ as alkylene may be linear or branched and contains preferably 2 to 12 carbon atoms. Illustrative examples are ethylene and the isomers of propylene, butylene, pentylene, hexylene, heptylene, octylene, nonylene, decylene, undecylene, dodecylene, tridecylene, tetradecylene, hexadecylene and octadecylene. Preferably $R_4$ is linear or branched alkylene of 3 to 12 carbon atoms, typically 1,3-propylene or 1,11-undecylene.

$R_5$ is preferably $C_1$-$C_4$alkyl and, most preferably methyl or ethyl.

The compounds of formula I are preferably obtained in the form of the optical R,R- and S,S-isomers, with respect to the position of the phosphine(methyl) groups.

In a particularly preferred embodiment of the compounds of formula I, $R_1$ is phenyl, $R_2$ is methyl or ethyl, $R_3$ is linear $C_2$-$C_4$alkylene, preferably 1,3-propylene, $R_4$ is linear $C_3$-$C_6$alkylene and $R_5$ is methyl or ethyl.

The invention further relates to a process for the preparation of compounds of formula I, which comprises reacting a compound of formula II

(II), wherein $R_4$ and $R_5$ are as previously defined, with a compound of formula III

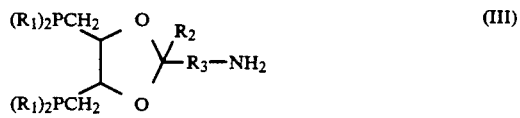

(III)

wherein $R_1$, $R_2$ and $R_3$ are as previously defined.

The compounds of formula II are known and some are commercially available, or they can be prepared by a process as described in FR-A-1 371 405. The compounds of formula III are novel and can be prepared by the following analogous processes.

The reaction of an alkali metal imide, such as lithium, sodium or potassium phthalimide, with an appropriate haloketone, such as chloro- or bromoketone, gives the corresponding imide ketones which are derivatised to the ketals, conveniently with methyl orthoformate. The ketal is subsequently reacted with the known 2,3-dihydroxy-1,4-bis(diphenylphosphine)butane and afterwards the compounds of formula III are prepared by hydrolysis or transimidation with, conveniently, hydrazine hydrate. Further particulars will be found in the working Examples. The invention also relates to the compounds of formula III, wherein $R_1$, $R_2$ and $R_3$ are as previously defined.

The reaction of the isocyanates of formula II with the compounds of formula III can be carried out at room temperature or elevated temperature, as in the range from 0° to 150° C. The concurrent use of a solvent is expedient, for example a hydrocarbon (petroleum ether, pentane, hexane, cyclohexane, methyl cyclohexane, benzene, toluene or xylene), or a halogenated hydrocarbon (methylene chloride, chloroform, 1,1,2,2-tetrachloroethane and chlorobenzene). An excess of isocyanate can be removed after the reaction by the reaction with an alkanol. The isolation and purification of the inventive compounds can be effected by conventional methods, as by distillation or chromatographic methods.

The inventive compounds are normally oily liquides which can be used as chiral ligands for iridium(II) and rhodium(II) complex salts which are excellent homogeneous enantioselective hydrogenation catalysts. The preparation of such catalysts is disclosed, inter alia, in U.S. Pat. No. 4,994,615. The inventive compounds are particularly suitable for preparing heterogeneous and enantioselective hydrogenation catalysts which are fixed on a solid carrier material.

The invention further relates to a solid carrier material which contains diphosphine rhodium or iridium complexes fixed on the surface thereof, which carrier material has the formula IV or IVa

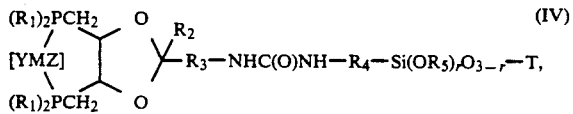

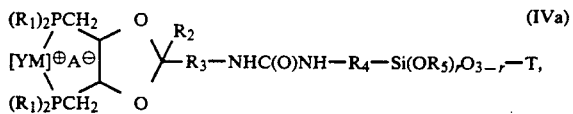

wherein Y denotes two monoolefin ligands or a diene ligand, M is Ir(I) or Rh(I), Z is —Cl, —Br or —I, $A^{\ominus}$ is the anion of an oxyacid or complex acid, T is a solid carrier material, r is 0, 1 or 2, and $R_1$, $R_2$, $R_3$, $R_4$ and $R_5$ are as previously defined. $R_1$, $R_2$, $R_3$, $R_4$ and $R_5$ have the same preferred meanings as given for the compounds of formula I.

A monoolefin ligand Y contains preferably 2 to 6, most preferably 2 to 4, carbon atoms. Illustrative examples are hexene, pentene, butene, propene and, preferably, ethene. A diene ligand Y contains preferably 4 to 8, most preferably 6 to 8, carbon atoms. The dienes may be open-chain or cyclic dienes whose olefin groups are preferably linked through one or two carbon atoms. Preferred dienes are 1,5-hexadiene, 1,5-cyclooctadiene and norbornadiene.

Z in formula IV is preferably —Cl or —Br. $A^{\ominus}$ in formula IVa is preferably $ClO_4^{\ominus}$, $CF_3SO_3^{\ominus}$, $BF_4^{\ominus}$, $B(phenyl)_4^{\ominus}$, $PF_6^{\ominus}$, $SbCl_5^{\ominus}$, $AsF_6^{\ominus}$ or $SbF_6^{\ominus}$.

The solid carrier material is preferably selected from glass, silicates and semimetals or metal oxides which are most preferably in the form of powders having average particle diameters of 10nm to 2000 μm, preferably 10 nm to 1000 μm and, most preferably, 10 nm to 500 μm. The particles may be compact as well as porous particles. Porous particles preferably have high inner surface areas, typically 1 to 1200 m², preferably 30 to 600 m². Exemplary of oxides and silicates are $SiO_2$, $TiO_2$, $ZrO_2$, $MgO$, $NiO$, $WO_3$, $Al_2O_3$, $La_2O_3$, silica gels, clays and zeoliths. A suitable solid carrier material is also activated carbon. Further, the solid carrier material may also be formed by polysiloxanes which are obtainable by condensing compounds of formula I by themselves or together with alkoxysilanes. Preferred carrier materials are silica gels, aerosils, alumina, titanium oxide and mixtures thereof. Exemplary of a suitable glass carrier material is commercially available controlled pore glass.

The modified carrier material of this invention can be obtained by reacting a solid carrier material which contains diphosphines fixed on the surface thereof and has the formula

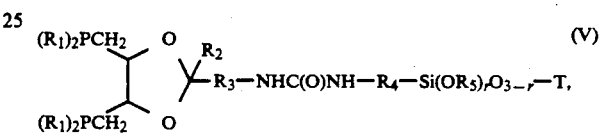

wherein $R_1$, $R_2$, $R_3$, $R_4$, $R_5$, T and r are as previously defined, with a metal compound of formula $[M(Y)Z]_2$ or $M(Y)_2^{\oplus}A^{\ominus}$, wherein M, Y, Z and $A^{\ominus}$ are as previously defined.

The reaction is preferably carried out in an inert gas atmosphere, as under argon, and conveniently in the temperature range from 0° to 40° C., preferably at room temperature. The concurrent use of a solvent or mixture of solvents is advantageous, conveniently selected from the group consisting of hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, ethylene glycol dimethyl ether) or mixtures thereof.

The novel modified material is also obtainable by direction of a hydroxyl group containing solid material, a compound of formula I and a metal compound of formula $[M(Y)Z]_2$ or $M(Y)_2^{\oplus}A^{\ominus}$. The reaction can be carried out stepwise by first adding a solution of the compound of formula I to the solid material, followed by the addition of a solution of the metal compound, or by first dissolving the compound of formula I and the metal compound im a solvent and adding this solution to the solid material. The reaction conditions may be those described previously or hereinafter in connection with the preparation of the material of formula V. The novel modified material can be isolated by filtration and purified by washing with an alkanol and dried under vacuum.

The novel modified material can also be prepared in situ prior to hydrogenation and then used direct as hydrogenation catalyst.

The invention further relates to the solid material of formula V. It can be prepared by reacting compounds of formula I with a hydroxyl group containing carrier material, advantageously in an inert gas atmosphere, as under argon, and in the temperature range from 40° to 180° C. The procedure preferably comprises charging the solid material to a reactor, adding a solution of the compound of formula I, and stirring the mixture at elevated temperature, conveniently in the range from 50° to 110° C. Suitable solvents are those mentioned above. The product is isolated either by decantation or filtration. The residue can be purified by washing with an alkanol and is then dried under a high vacuum.

The novel modified material is preeminently suitable for use as heterogeneous catalyst for the enantioselective hydrogenation of compounds containing prochiral carbon double bonds and carbon/hetero atom double bonds, typically compounds which contain a group selected from C=C, C=N, C=O, C=C—N and C=C—O (q.v. K. E. König, The Applicability of Asymmetric Homogeneous Catalysis, in James D. Morrison (ed.), Asymmetric Synthesis, Vol. 5, Academic Press, 1985). Examples of such compounds are prochiral imines and ketones. The novel catalysts can be separated almost completely from the reaction mixture after the reaction in simple manner, as by decantation of filtration, and subsequently reused. Compared with other known homogeneous catalysts, there is no or only a minor loss of activity which if desired, can be compensated for by adding minor amounts of fresh catalyst. Furthermore, selectivities (optical yields) are obtained comparable to those of homogeneous catalysts. In the hydrogenation of N-arylketimines with novel iridium catalysts, it has surprisingly been found that, along with comparable selectivities, the novel catalysts even exhibit a higher catalytic activity and a substantially lower deactivation than the homogeneous iridium catalysts disclosed in U.S. Pat. No. 4,994,615 and EP-A-0 301 457.

In another of its aspects, the invention relates to the use of the solid carrier material of formulae IV or IVa as heterogeneous catalyst for the asymmetrical hydrogenation of prochiral compounds containing carbon double bonds or carbon/hetero atom double bonds, especially those containing a C=C, C=N, C=O, C=C—N or C=C—O group. The use for hydrogenating unsymmetrical carbon double bonds, ketimines and ketones is preferred. It is also preferred to use the novel solid carrier material of formulae IV or IVa obtained in the form of the iridium catalyst for hydrogenating prochiral N-arylketimines to optically active secondary amines. The novel solid carrier material of formulae IV or IVa obtained in the form of the rhodium catalyst is preferably used for hydrogenating carbon double bonds, as for example prochiral carbon double bonds.

In yet another of its aspects, the invention relates to a process for the asymmetrical hydrogenation of compounds containing carbon double bonds or carbon/hetero atom double bonds, which comprises hydrogenating said compounds in the temperature range from −20° to +80° C. and under a hydrogen pressure of $10^5$ to $10^7$ Pa, in the presence of catalytic amounts of a solid carrier material of formula IV or IVa.

Surprisingly, it has also been found that, compared with the corresponding monomeric iridium catalysts which are virtually inactive after a hydrogenation, iridium catalysts based on the fixable ligands described by I. Kolb et al. in React. Kinet. Catal. Lett. 7(2), pages 199 to 204 (1977), suffer only a minor loss of activity.

The invention further relates to carrier materials of formulae VI and VIa

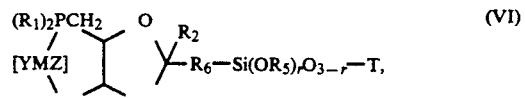

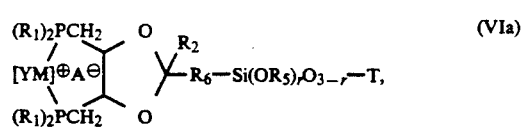

wherein $R_1$, $R_2$, $R_5$, Y, Z, $A^\ominus$, T and r are as previously defined, including the preferred meanings, M is iridium(I) and $R_6$ is linear or branched $C_2$-$C_{18}$alkylene.

$R_6$ is preferably linear or branched $C_2$-$C_{12}$alkylene, most preferably $C_2$-$C_{10}$alkylene, typically 1,3-propylene, 1,4-butylene, 1,5-pentylene and 1,6-hexylene.

The carrier materials of formulae VI and VIa can be prepared by the processes described hereinbefore. The silanes used for their preparation can be conveniently obtained by the process described by I. Kolb et al. in React. Kinet. Catal. Lett. 7(2), pages 199 to 204 (1977).

In yet another of its aspects, the invention relates to the use of the solid carrier material of formula VI or VIa as heterogeneous catalyst for the asymmetrical hydrogenation of prochiral N-arylketimines to optically active secondary amines.

The invention further relates to a process for the asymmetrical hydrogenation of prochiral N-arylketimines to optically active secondary amines, which comprises hydrogenating the N-arylketimines in the temperature range from −20° to +80° C. and under a hydrogen pressure of $10^5$ to $10^7$ Pa in the presence of catalytic amounts of a solid carrier material of formula VI or VIa.

Preferred unsaturated compounds have already been mentioned. Unsymmetrical ketimines and ketones are known. Suitable N-arylketimines are disclosed, for example, in EP-A-0 256 982. N-Aliphatic ketimines are disclosed, for example, in EP-A-0 301 457. Such imines can be prepared from the corresponding unsymmetrical ketones, which are known and in some cases commercially available or obtainable by known processes. Suitable unsubstituted or substituted alkenes are described in the publication by K. E. König cited above.

The process is preferably carried out in the temperature range from −20° to +50° C. and preferably under a hydrogen pressure of $1 \cdot 10^5$ to $6 \cdot 10^6$ Pa.

The amount of catalyst will preferably be chosen such that the molar ratio of compound to be hydrogenated to active catalyst component fixed on the solid carrier material is preferably from 2000 to 40, most preferably 800 to 50.

A preferred process comprises additionally using an ammonium or alkali metal chloride, bromide or iodide, especially when using novel iridium catalysts. The amount may be from 0.1 to 100, preferably 1 to 50 and, most preferably, 2 to 20, equivalents, based on the active catalyst component fixed on the solid carrier material. The addition of iodides is preferred. Ammonium is preferably tetraalkylammonium containing 1 to 6 carbon atoms in the alkyl moieties. The preferred alkali metal is lithium, sodium or potassium.

The hydrogenation can be carried out without or in the presence of solvents. Suitable solvents, which may be used alone or in admixture, are typically: aliphatic and aromatic hydrocarbons (pentane, hexane, cyclohexane, methylcyclohexane, benzene, toluene, xylene); alcohols (methanol, propanol, butanol, ethylene glycol monomethyl ether); ethers (diethyl ethers, diethylene glycol dimethyl ether, tetrahydrofuran, dioxane); halogenated hydrocarbons (methylene chloride, chloroform, 1,1,2,2-tetrachloroethane, chlorobenzene); carboxylates and lactones (ethyl acetate, butyrolactone, valerolactone); N-substituted acid amides and lactams (dimethyl formamide, N-methylpyrrolidine). Mixtures of an aromatic hydrocarbon and an alcohol, for example toluene/ethanol or benzene/methanol are advantageous.

By means of the inventive hydrogenation process it is possible to obtain optically pure compounds which are useful intermediates for the synthesis of biologically active compounds, especially in the pharmaceutical and agrochemical sectors. Thus, for example, herbicidally active 5-imidazolecarboxylic acid derivatives which can be used for weed control (EP-A-0 207 563) can be obtained from amines, especially N-carbalkoxymethylamines. The optically pure α-aminocarboxylic acid esters are suitable for peptide syntheses.

The following Examples illustrate the invention in more detail. The reactions are carried out under argon. The NMR spectra are recorded with a 250 Mhz spectrophotometer.

A) PREPARATION OF THE STARTING MATERIALS

Example A1

N-[2,3-O-(5'-Amino-2'-pentylidene)-2,3-hydroxy-1,4-bis(diphenylphosphine)-butane]-N'-[3-triethoxysilyl-prop-yl]-urea a) Preparation of 5-phthalimidyl-2,2-dimethoxypentane.

18.5 g (0.1 mol) of potassium phthalimide and a trace of potassium iodide are added to a solution of 11.5 ml (0.1 mol) of 5-chloro-2-pentanone in 100 ml of dimethyl formamide and the mixture is stirred initially for 15 hours at 90° C. and then for 5 hours at 110° C. After cooling, the mixture is taken up in 300 l of water/100 ml of chloroform, the organic phase is separated, and the aqueous phase is extracted with 3×30 ml of chloroform. The organic phase is then washed with 2×50 ml of 0.2N NaOH and then with 2×25 ml of water and dried over MgSO$_4$. The solvent is stripped off and the residue is dried under a high vacuum, giving 16.6 g of a solid yellow residue, from which, after treatment with diphenyl ether, 14 g of 5-phthalimidyl-2-pentanone are isolated in the form of a white powder. 8.3 g of this powder are dissolved in 40 ml of methanol and to the solution are added 4.34 ml (0.04 mol) of methyl orthoformate. Then 0.2 g of pyridinium toluenesulfonate are added and the mixture is stirred for 1 hour under reflux. The solvent is then removed on a rotary evaporator and the residue is extracted with 200 ml of water/diethyl ether (1:1) and thereafter repeatedly with a total of 100 ml of diethyl ether. The organic phase is washed with 2×25 ml of a saturated aqueous solution of sodium chloride, dried over potassium carbonate, and the solvent is removed on a rotary evaporator, giving 8.8 g of 5-phthalimidyl-2,2-dimethoxypentane as a viscous oil, which can be reused direct.

b) Preparation of (−)-2,3-O-(5'-phthalimidyl-2'-pentylidene)-2,3-hydroxy-1,4-bis(diphenylphosphine)-butane.

8.8 g (32 mmol) of 5-phthalimidyl-2,2-dimethoxypentane in 50 ml of toluene and 350 mg of p-toluenesulfonic acid monohydrate are added to a solution of 4.3 g (9.4 mmol) of (−)-2,3-dihydroxy-1,4-bis(diphenylphosphine)methylbutane in 150 ml of toluene, and the mixture is slowly heated to an external temperature of 120°-130° C. Afterwards, methanol is distilled from the reaction mixture until the boiling point of toluene is reached. The batch is cooled and the toluene is removed on a rotary evaporator. The residue is chromatographed twice (Merck 60 silica gel, 1st eluant toluene, 2nd eluant toluene/diethyl ether 1:1), giving 3.9 g (58%) of (−)-2,3-O-(5'-phthalimidyl-2'-pentylidene)-2,3-hydroxy-1,4-bis-(diphenylphosphine)-butane as a colourless viscous oil. $^{31}$P-NMR (CDCl$_3$): −23.22 (s) and −23.82 (s).

c) 330 μl (6.8 mmol) of hydrazine hydrate are added dropwise to 3.8 g of (−)-2,3-O-(5'-phthalimidyl-2'-pentylidene)-2,3-hydroxy-1,4-(diphenylphosphine)-butane in 40 ml of methanol and the mixture is heated to 100° C., whereupon a white precipitate slowly forms. After 5 hours, a further 150 μl of hydrazine hydrate are added dropwise and the batch is stirred for 19 hours. The resultant suspension is cooled, diluted with 50 ml of methanol and filtered. The residue is washed with 50 ml of ethanol, and the filtrate is concentrated by evaporation on a rotary evaporator at 40° C. under vacuum. The residue is taken up in 50 ml of methylene chloride and the solution is filtered. The residue is washed with 25 ml of methylene chloride, and the filtrate is concentrated by evaporation on a rotary evaporator, giving a viscous oil which is purified by chromatography (Merck 60 silica gel, elution with tetrahydrofuran/triethylamine 10:1). Yield: 2.94 g (80%) of (−)-2,3-O-(5'-amino-2'-pentylidene)-2,3-hydroxy-1,4-bis(diphenylphosphine)-butane as a colourless viscous oil: $^{31}$P-NMR (CDCl$_3$): −23.106 (s), −23.177 (s). $^1$H-NMR (CDCl$_3$): 2.6 (t, 2H, CH$_2$N).

d) 77.5 μl (0.31 mmol) of 1-triethoxysilyl-3-isocyanatopropane are added dropwise to a solution of 150 mg (0.277 mmol) of (−)-2,3-O-(5'-amino-2'-pentylidene)-2,3-hydroxy-1,4-bis(diphenylphosphine)-butane in 5 ml of toluene, and the mixture is stirred for 20 hours at room temperature. The solvent is then removed on a rotary evaporator and the residue is dried under a high vacuum, giving 210 mg (96%) of the title compound, N-[2,3-O-(5'-amino-2'-pentylidene)-2,3-hydroxy-1,4-bis(diphenylphosphine)-butane]-N'-[3-triethoxysilyl-prop-yl]-urea, as an oil which is used without further purification in the subsequent reactions. $^{31}$P-NMR (CDCl$_3$): δ−23.12 (s), −23.44 (s); $^1$H-NMR (CDCl$_3$): δ1.29 (s, 3H, CH$_3$)

B) PREPARATION OF CARRIER MATERIALS WITH FIXED LIGANDS

Example B1

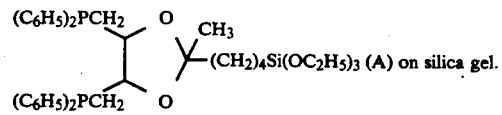

With stirring, 10 g of silica gel (Merck 100) are dried at 130° C. under a high vacuum and then cooled to room temperature under argon. Then a solution of 1 g of compound (A), the title compound of Example A1, in 60 ml of dry, degassed toluene are added and the mixture is slowly stirred for 5.5 hours at 70° C. After cooling, the supernatant solution is removed by vacuum filtration from the silica gel, which is washed 5 times with degassed methanol and subsequently dried at 30° C. under a high vacuum. Elemental analysis shows a phosphorus content of 0.37%, corresponding to 60 μmol of fixed compound (A) per g of silica gel.

Example B2

Compound A1 on silica gel.

With stirring, 3 g of silica gel (Merck 100) are dried at 130° C. under a high vacuum and then cooled to room temperature under argon. Then a solution of 330 mg of compound A1 in 14 ml of dry toluene is added and the mixture is slowly stirred for 5 hours at 70° C. After cooling, the supernatant solution is removed by vacuum filtration from the silica gel, which is washed 5 times with degassed methanol and subsequently dried at 30° C. under a high vacuum. Elemental analysis shows a phosphorus content of 0.54%, corresponding to 86 μmol of fixed compound A1 per g of silica gel.

C) USE EXAMPLES

Example C1

Hydrogenation with iridium catalyst.

5.4 μmol of [Ir(cyclooctadiene)Cl]$_2$, 13 μmol of the carrier material of Example B1 and 2 equivalents of tetra-n-butylammonium iodide/mol of Ir are charged, under argon, to a round flask together with 2 ml of methanol and 2 ml of benzene, and the mixture is stirred until the solution is decolourised. Then a solution of 1033 mg of N-(2,6-dimethylphen-1-yl)methoxymethyl methylketimine in 1.5 ml of methanol and 1.5 ml of benzene is added dropwise and the mixture is introduced under pressure into a 50 ml steel autoclave. The mixture is evacuated and flushed with hydrogen three times, and the hydrogen pressure is finally set to 4.10$^6$ Pa. The batch is stirred at 30° C. and the course of the hydrogenation is followed by observing the drop in pressure. The conversion is analysed by gas chromatography. The catalyst is isolated by filtration and the solvent is stripped from the reaction solution on a rotary evaporator under vacuum. The crude product is purified by flash chromatography (silica gel, hexane/methyl acetate 1:1) and the enantiomer excess is determined by polarimetry (rotation of the (S)-enantiomer [α]$_{365}$ at 20° C.-130.5°, c=3 in hexane). The conversion after 12 hours is 99.3%, ee 61.9%. Reuse of the catalyst: The supernatant solution is stripped from the catalyst, the same amount of ketimine and tetra-n-butylammonium iodide as before is added and the same procedure is carried out. The conversion after 28 hours is 99.7%, ee 59.9%.

Example C2

Hydrogenation with Ir catalyst prepared in situ.

155 mg (0.0105 mmol) of the carrier material of Example B2 are weighed into a flask under argon. In a second flask, 0.0052 mmol of [Ir(cyclooctadiene)Cl]$_2$ and 0.016 mmol of tetra-n-butylammonium iodide are dissolved under argon in 2 ml of methanol/benzene (1:1), and the solution is added dropwise to the carrier material in the first flask. The mixture is stirred until the solution is decolourised. Then a solution of 1033 mg (5.4 mmol) of N-(2,6-dimethylphen-1-yl)methoxymethyl methylketimine (purity 98.5%) in 5 ml of methanol/benzene is added dropwise, also under argon, and the mixture is introduced under pressure into a steel autoclave. The hydrogenation is carried out at a hydrogen pressure of 4.10$^6$ Pa and 30° C. After 19 hours the hydrogenation is discontinued and the autoclave is placed under argon. The reaction solution is drawn off from the catalyst with a syringe and worked up as described in Example C1. The conversion is 92.5%, ee 62.2%.

Reuse of the catalyst: A solution of 5.4 mmol of ketimine and 0.016 mmol of tetra-N-butylammonium iodide in 7 ml of methanol/benzene (1:1) is added and further hydrogenation is carried out as described in the previous reaction. The hydrogenation is discontinued after 23 hours, although the catalyst still hydrogenates with constant activity. The conversion is 59.1%, ee 59.7%.

Example C3

Hydrogenation with rhodium catalyst.

182 mg (0.0156 mmol) of the carrier material of Example B2 are weighed into a round flask under argon and, in a second round flask, 0.0125 mmol of [Rh(cyclooctadiene)$_2$]BF$_4$ are dissolved, under argon, in 1 ml of methanol. The solution is then added dropwise to the carrier material in the first flask. The mixture is stirred until the solution is decolourised. To this mixture is then added, under argon, a solution of 2.5 mmol of methyl (Z)-acetamidocinnamate in 17.5 ml of methanol and 4 ml of tetrahydrofuran. The mixture is evacuated and flushed three times with hydrogen, and the hydrogen pressure is set to 10$^5$ Pa. The batch is stirred vigorously. The conversion is 100% after 15 minutes, ee 67.4%.

Reuse of the catalyst: The reaction solution is stripped from the catalyst. Then a solution of 2.5 mmol of methyl (Z)-acetamidocinnamate in 17.5 ml of methanol and 5 ml of tetrahydrofuran is added. The mixture is evacuated and flushed three times with hydrogen, and the hydrogen pressure is set to 10$^5$ Pa. The batch is stirred vigorously. The conversion is 100% after 10 minutes, ee 69.6%.

What is claimed is:

1. A compound of formula

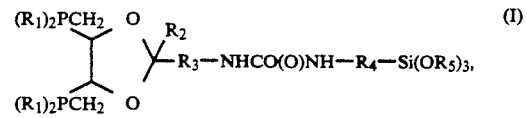

wherein R$_1$ denotes identical or different radicals and is linear or branched C$_1$-C$_{12}$alkyl, unsubstituted C$_5$-C$_6$cycloalkyl or C$_5$-C$_6$cycloalkyl which is substituted by C$_1$-C$_4$alkyl or C$_1$-C$_4$alkoxy, or is phenyl or benzyl, or both substituents R$_1$ of a group (R$_1$)$_2$P are o,o'-diphenylene, R$_2$ is hydrogen, linear or branched C$_1$-C$_{12}$alkyl, phenyl or benzyl, R$_3$ is C$_1$-C$_{12}$alkylene, R$_4$ is C$_2$-C$_{18}$alkylene, phenylene or benzylene, and R$_5$ is C$_1$-C$_6$alkyl or phenyl.

2. A compound according to claim 1 of formula I, wherein R$_1$ is phenyl.

3. A compound according to claim 1 of formula I, wherein R$_2$ as alkyl contains 1 to 6 carbon atoms.

4. A compound according to claim 1 of formula I, wherein R$_3$ is linear or branched C$_1$-C$_8$alkylene.

5. A compound according to claim 1 of formula I, wherein R$_4$ is linear or branched C$_2$-C$_{12}$alkylene.

6. A compound according to claim 1 of formula I, wherein R$_5$ is methyl or ethyl.

7. A compound according to claim 1 which is in the form of the R,R- or S,S-isomers, with respect to the position of the phosphine(methyl) groups.

8. A compound according to claim 1 of formula I, wherein R$_1$ is phenyl, R$_2$ is methyl or ethyl, R$_3$ is linear C$_2$-C$_4$alkylene, R$_4$ is linear C$_3$-C$_6$alkylene and R$_5$ is methyl or ethyl.

* * * * *